(12) United States Patent
List et al.

(10) Patent No.: US 9,783,561 B2
(45) Date of Patent: Oct. 10, 2017

(54) CHIRAL IMIDODIPHOSPHATES AND DERIVATIVES THEREOF

(71) Applicant: STUDIENGESELLSCHAFT KOHLE MBH, Mülheim an der Ruhr (DE)

(72) Inventors: Benjamin List, Mülheim an der Ruhr (DE); Ilija Coric, Mülheim an der Ruhr (DE); Sreekumar Vellalath, College Station, TX (US)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 14/371,238

(22) PCT Filed: Jan. 8, 2013

(86) PCT No.: PCT/EP2013/050189
§ 371 (c)(1),
(2) Date: Jul. 9, 2014

(87) PCT Pub. No.: WO2013/104604
PCT Pub. Date: Jul. 18, 2013

(65) Prior Publication Data
US 2014/0350268 A1    Nov. 27, 2014

(30) Foreign Application Priority Data
Jan. 10, 2012 (EP) .................................... 12150663

(51) Int. Cl.
| | |
|---|---|
| *C07F 9/6574* | (2006.01) |
| *B01J 31/02* | (2006.01) |
| *C07F 9/6571* | (2006.01) |
| *C07D 493/10* | (2006.01) |
| *C07D 319/08* | (2006.01) |
| *C07D 327/06* | (2006.01) |
| *C07D 339/08* | (2006.01) |
| *C07D 239/90* | (2006.01) |
| *C07C 231/06* | (2006.01) |
| *C07D 209/08* | (2006.01) |
| *C07D 209/12* | (2006.01) |
| *C07D 307/10* | (2006.01) |
| *C07D 307/20* | (2006.01) |

(52) U.S. Cl.
CPC ....... *C07F 9/65746* (2013.01); *B01J 31/0264* (2013.01); *B01J 31/0271* (2013.01); *C07C 231/06* (2013.01); *C07D 209/08* (2013.01); *C07D 209/12* (2013.01); *C07D 239/90* (2013.01); *C07D 307/10* (2013.01); *C07D 307/20* (2013.01); *C07D 319/08* (2013.01); *C07D 327/06* (2013.01); *C07D 339/08* (2013.01); *C07D 493/10* (2013.01); *C07F 9/65744* (2013.01); *C07F 9/657154* (2013.01); *B01J 2231/52* (2013.01); *B01J 2231/70* (2013.01)

(58) Field of Classification Search
CPC .................................................... C07F 9/6574
See application file for complete search history.

(56) References Cited

FOREIGN PATENT DOCUMENTS

EP    1 623 971 A1    2/2006

OTHER PUBLICATIONS

Hellwig, et al; "A simple protocol for the synthesis of chiral bidentate imidodiphosphoric tetramide ligands: application in the metal-free asymmetric allylation of aldehydes"; Tetrahedron Letters 42 (2001) 5417-5419.
Coric et al; "Asymmetric spiroacetalization catalysed by confined Bronsted acids" Nature, vol. 483; Mar. 2012; 315-319.
International Search Report and Written Opinion for corresponding application PCT/EP2013/050189 mailed May 10, 2013.
Xu, F. et al. SPINOL-Derived Phosphoric Acids: Synthesis and Application in Enantioselective Friedel-Crafts Reaction of Indoles with Imines. J. Org. Chem. 75, 8677-8680 (2010).
Ćorić, I.,Müller, S. & List, B. Kinetic Resolution of Homoaldols via Catalytic Asymmetric Transacetalization. J. Am. Chem. Soc. 132, 17370-17373 (2010).

*Primary Examiner* — Noble Jarrell
*Assistant Examiner* — John S Kenyon
(74) *Attorney, Agent, or Firm* — Norris, McLaughlin & Marcus, P.A.

(57) ABSTRACT

The invention relates to chiral imidodiphosphates and derivatives thereof having the general formula I,

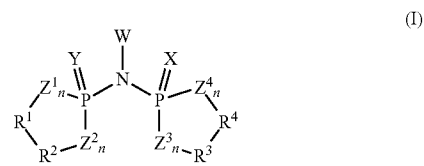

The compounds are suitable as chiral Brønsted acid catalysts, phase-transfer catalysts, chiral anions for organic salts, metal salts or metal complexes for catalysis.

17 Claims, No Drawings

CHIRAL IMIDODIPHOSPHATES AND DERIVATIVES THEREOF

This application is a 371 of PCT/EP2013/050189, filed Jan. 8, 2013, which claims foreign priority benefit under 35 U.S.C. §119 of the European Patent Application No. 12150663.8, filed Jan. 10, 2012, the disclosures of which are incorporated herein by reference.

The present invention relates to chiral imidodiphosphates, their salts and metal complexes as well as derivatives thereof and their use as catalysts.

Many chemical transformations are catalyzed by Brønsted acids. In enantioselective organocatalysis, this possibility of metal-free, and in the case of chiral Brønsted acids also enantioselective, catalysis is a rapidly growing field with increasing applications. In this field of organocatalysis, a distinction is made between hydrogen bonding catalysts such as thioureas and also TADDOL and BINOL derivatives and stronger Brønsted acids such as phosphoric acid diesters and derivatives thereof as disclosed in EP 1623971. Bulky phosphates have found wide application in asymmetric catalysis, however, it is challenging to further modify their steric environment because, for example, 3,3'-substituents on BINOL radiate away from the active site. Significant synthetic efforts have been undertaken by a number of groups to design alternative backbones that would narrow the chiral environment of the phosphoric acid as discussed in Xu, F. et al. SPINOL-Derived Phosphoric Acids: Synthesis and Application in Enantioselective Friedel-Crafts Reaction of Indoles with Imines. J. Org. Chem. 75, 8677-8680 (2010) and Čorić, I., Müller, S. & List, B. Kinetic Resolution of Homoaldols via Catalytic Asymmetric Transacetalization. J. Am. Chem. Soc. 132, 17370-17373 (2010).

While the fields of chiral Brønsted acid catalysis and chiral anion directed catalysis have acquired wide popularity and importance in recent years, numerous transformations are still elusive, in particular reactions of small substrates that do not posses sterically demanding protecting groups, large aromatic/planar surfaces, or bulky substituents are still extremely rare. Furthermore reactions including substrates or intermediates lacking spatially defined interactions such as hydrogen bonding with the catalyst are very limited. The reason for these limitations, at least in part, is the inability of current synthetic Brønsted acid catalysts and their respectful anions to provide more variable as well as truly compact chiral microenvironments.

The preparation of synthetic Brønsted acid catalysts that display readily tuneable steric environment, as well as the potential for highly sterically demanding chiral microenvironment around their active site is therefore desirable.

The present invention provides such new Brønsted acid catalysts by means of new chiral imidodiphosphates, a simple process for preparing chiral imidodiphosphates and also their use in catalysis.

On the field of Lewis-base promoted catalysis, imidodiphosphoric tetramide ligand system as a catalytic unit has been disclosed by Hellwig et al. in Tetrahedron Letters 42 (2001), p. 5417-19. Said catalytic system has been reported to be useful for the allylation of aldehydes with trichlorosilane in such a Lewis-base promoted catalysis only. Said ligand structures were not shown to possess beneficial properties, such as improved enantioselectivity, compared to other Lewis base catalysts. Said Lewis-base catalytic systems cannot promote Brønsted acid catalysed and chiral-anion-directed reactions and are thus of limited value for a number of catalytic reactions for which the specific catalytic system of the present invention is suitable.

The unknown cyclic imidodiphosphates according to the present invention and the substituted derivatives thereof can be classified as strong Brønsted acids. The conjugated bases of the imidodiphosphates are likewise suitable as chiral anions in enantioselective catalysis.

Thus, the present invention provides chiral imidodiphosphates and derivatives thereof having the general formula (I)

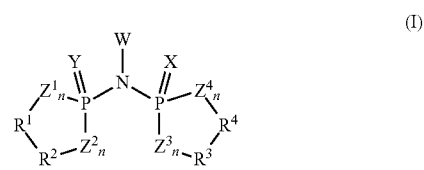

wherein:

X and Y may be, independently from each other, the same or different and represent O, S, Se and $NR^N$, $Z^1$ to $Z^4$ may be, independently from each other, the same or different and represent O, S, Se and $NR^N$, n stands for 0 or preferably 1, W is a substituent being capable of forming an ionic bond with the imidodiphosphate moiety, $R^1$ to $R^4$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups whereby $R^1$ and $R^2$ are forming a ring system with $Z^1$ and $Z^2$ and $R^3$ and $R^4$ are forming a ring system with $Z^3$ and $Z^4$, respectively, and $R^N$ may be selected from hydrogen, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or heterosubstituents, including its tautomeric and ionic forms, and derivatives thereof.

The inventors have found out that by forming two ring systems around the imidodiphoshate moiety of the chiral compound, the catalytic site thereof can be protected and is perfectly suitable for highly selective catalytic reactions.

In the following, it is to be understood that the above formula (I) comprises its tautomeric forms as represented by the formulae (Ia) or (Ib)

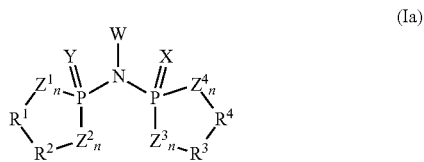

-continued

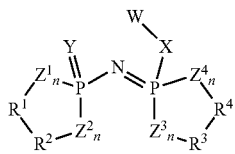

wherein X, Y, $Z^1$ to $Z^4$, n, W, $R^1$ to $R^{4'}$ and $R^N$ have the meaning as defined above. In the following, it is to be understood that any of the formulae (II), (Ill), (IV) and (V) below comprises its respective tautomeric forms as represented by formula (Ia) or formula (Ib).

In the context of this invention, W is a substituent being capable of forming an ionic bond with the imidodiphosphate moiety. In this respect, the tautomeric forms as well as polarized bonds $W^+$—$N^-$ are understood to be covered by said definition.

In the present application, the expression "imidodiphosphates" is to be understood to comprise derivatives thereof, wherein one or more of the oxygen atoms of the imidodiphosphate moiety is replaced by S, Se, $NR^N$ as defined above.

In the above formula (I) and the derived formulae below, it is to be understood that any tautomeric form of the inventive chiral imidodiphosphates as well as any charged form thereof including any anionic form is to be comprised by the representation of said formula. It is also to be understood that imidodiphosphates could possess inherent chirality even if all of the groups $R^1$ to $R^4$ are achiral groups.

In the above formulae (I), $R^1$ to $R^4$ may be selected each from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or heterosubstituents.

In the above formula (I), W is a substituent being capable of forming an ionic bond with the imidodiphosphate moiety such as hydrogen, halogen, a metal such as Li, Na, K, Rb, Cs, Be, Mg, Ca, Sr, Ba, Sc, Ti, V, Cr, Mn, Fe, Co, Ni, Cu, Zn, Y, Zr, Mo, Ru, Rh, Pd, Ag, W, Re, Os, Ir, Pt, Au, Al, Pb, La, Sm, Eu, Yb, U, or a cationic organic group as exemplified in Scheme 2 below. or a substituted silicon such as —$SiR^IR^{II}R^{III}$, wherein $R^I$, $R^{II}$ and $R^{III}$ may be same or different and each stand for hydrogen, halogen, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or a heterosubstituent.

The expression "partially arene-hydrogenated forms thereof" is to be understood that in case that the aromatic structure comprises more than one aromatic cycle such as for naphthalene, at least one aromatic cycle, one aromatic cycle remaining, might be partially or fully hydrogenated.

The anionic form may be complemented by any cation for forming an ion pair.

In one embodiment of the above formulae (I), $Z^1$ to $Z^4$ represent O, n is 1 and the other definitions are as given before for formula (I), as represented by formula (II):

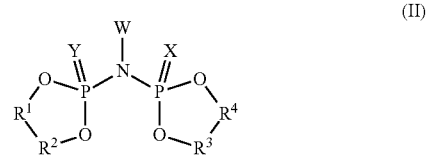

In such formulae (I) and (II), the moiety

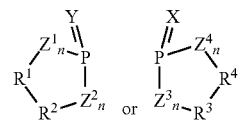

might be a five to ten-membered ring structure of ($R^1$, $R^2$, $Z^1$, $Z^2$ and —PY—) or ($R^3$, $R^4$, $Z^3$, $Z^4$ and —PX—), respectively.

In one embodiment of the compounds of formula (II), X and Y represent O and the other definitions are as given before for formulae (I), as represented by formula (III):

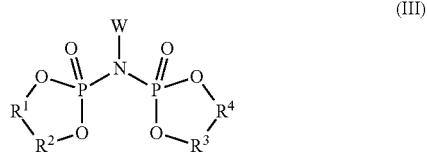

In such formula (III), at least one of ($R^1$ and $R^2$) and ($R^3$ and $R^4$) may form a ring structure derived from a bridged aromatic structure such as biphenyl optionally substituted, BINOL, TADDOL, VAPOL, SPINOL, 1,1'-binaphthalene, 1,1'-bianthracene, 1,1-biphenanthrene, as well as the partially arene-hydrogenated forms such as 8H-BINOL, each of said rings systems optionally being substituted by one or more substituents selected from heterosubstituents, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon such as aryl, aryl-($C_1$-$C_6$)-alkyl, heteroaryl-($C_1$-$C_6$)-alkyl, each hydrocarbon optionally being substituted by one or more heterosubstituents. In such formula (III), the ring structure formed by ($R^1$ and $R^2$) or ($R^3$ and $R^4$) may be the same or different.

In another embodiment, the compounds of formula (I) may be represented by formula (IV):

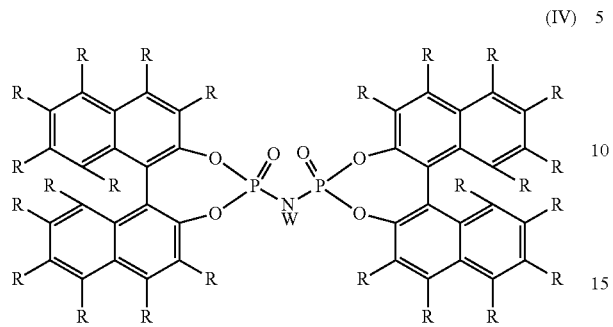
(IV)

In said formula (IV), the substituent R may be the same or different on each position and may each stand for hydrogen, a heterosubstituent, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or a heterosubstituent.

In said formula (IV), W is defined as given before for formula (I).

The substituents on the ring structure proximal to the —Z—P— bond, such as the —O—P-bond, are preferably bulky groups and may be selected from the definitions for $R^N$ or heterosubstituents.

Basically, any chiral groups are possible as chiral groups for the inventive compounds. If the other group in each case is not chiral, the groups $R_1$ to $R_4$ are any organic group which may be saturated or unsaturated, linear, cyclic or heterocyclic, aromatic and/or heteroaromatic.

Three examples of said compound having the formula (IV) are shown below:

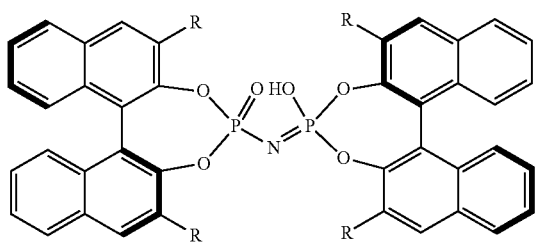
1

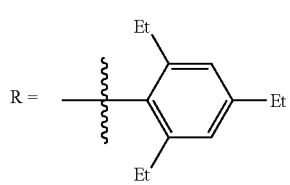

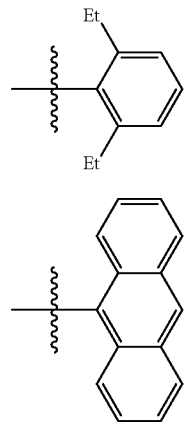
2

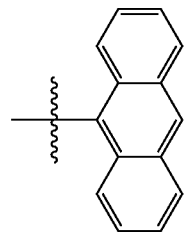
3

In organic synthesis, particularly in the synthesis of pharmaceutical active compounds, chiral compounds are frequently used as catalysts in order to obtain the desired product in a high enantiomeric purity or diastereomeric purity.

It has been found that the compounds according to the invention are well suited as catalysts for enantioselective synthesis. Here, they function as chiral Brønsted acids or the conjugated bases thereof as chiral anions in enantioselective catalyses directed by counterions.

The following definitions for the individual groups R, $R^N$, and $R^1$ to $R^4$ apply equally as follows.

A heterosubstituent as defined according to the invention can be selected from OH, F, Cl, Br, I, CN, $NO_2$, $SO_3H$, a monohalogenomethyl group, a dihalogenomethyl group, a trihalogenomethyl group, $CF(CF3)_2$, $SF_5$, amine bound through N atom, —O-alkyl (alkoxy), —O-aryl, —O—$SiR^S_3$, S—$R^S$, S(O)—$R^S$, $S(O)_2$—$R^S$, COOH, $CO_2$—$R^S$, amide, bound through C or N atom, formyl group, C(O)—$R^S$, COOM, where M may be a metal such as Na or K. $R^S_3$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups.

Aliphatic hydrocarbons including alkyl, alkenyl and alkinyl may comprise straight-chain, branched and cyclic hydrocarbons.

Heteroaliphatic is a hydrocarbon including alkyl, alkenyl and alkinyl which may comprise straight-chain, branched and cyclic hydrocarbons with one or more carbon atoms substituted with a heteroatom.

In more detail, $C_1$-$C_{20}$-Alkyl can be straight chain or branched and has 1, 2, 3, 4, 5, 6, 7, 8, 9, 10, 11, 12, 13, 14, 15, 16, 17, 18, 19 or 20 carbon atoms. Alkyl might be $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might be cyclopropyl, cyclobutyl, cyclopentyl, cyclohexyl or cycloheptyl. Alkenyl might be $C_2$-$C_{20}$ alkenyl. Alkinyl might be $C_2$-$C_{20}$ alkinyl.

Said unsaturated alkenyl- or alkinyl groups can be used for linking the inventive compounds to a carrier such as a polymer to serve for an immobilized catalyst.

Halogen is F, Cl, Br or I.

Alkoxy is preferably $C_2$-$C_{10}$ alkoxy such as methoxy, ethoxy, propoxy, tert-butoxy etc.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

Aryl might be phenyl, naphthyl or biphenyl.

Arylalkyl might be benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothia-zolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

In a preferred embodiment of the present invention as for example shown in formula (IV), at least one of R proximal to the —O—P— bond is not hydrogen and may be selected from among methyl, ethyl, isopropyl, cyclohexyl, cyclopentyl, phenyl, 2,4,6-triisopropylphenyl, 2,4,6-triethylphenyl, 2,6-diethylphenyl, 2,6-diethylphenyl, 2-isopropylphenyl, 5-methyl-2-isopropylphenyl, mesityl, 9-phenanthryl, 9-anthracenyl, ferrocenyl, N-(perfluorophenyl)acetamide, N-(4-chlorophenyl)acetamide, N-(naphthalen-1-yl)acetamide, N-benzhydrylacetamide, N-(2,6-diisopropylphenyl)acetamide, 1-anthracenyl, corannulene, porphyrin, 1-naphthyl, 2-naphthyl, 4-biphenyl, 3,5-(trifluoromethyl)phenyl, 2,6-dimethylphenyl, tert-butyl, tris-methylsilyl, tert-butydimethylsilyl, phenyldimethylsilyl, methyldiphenylsilyl, tris-mesitylsilyl, tris-phenylsilyl, 4-nitrophenyl and 2,6-methyl-4-butylphenyl, trifluoromethyl, unbranched (linear) and branched ($C_1$-$C_{12}$)-perfluoroalkyls, 3,4,5-trifluorophenyl, 1,3-bis(perfluoropropan-2-yl)phenyl, 1,3-bis(perfluorobutyl)phenyl and/or pentafluorophenyl and also chloride, iodide, fluoride, COOH, B(OH)$_2$, B(alkyl)$_2$, B(O-alkyl)$_2$, B(pinacol), BF$_3$X where X=Na or K, OTf. The other groups are preferably hydrogen.

The compounds according to the invention can be converted in process steps which are well known per se to those skilled in the art into organic salts, metal salts or metal complexes. In one possible embodiment, the imidodiphosphates are reacted with an appropriate metal salt, for example with the carbonate of the appropriate metal. Examples of organic salts, metal salts and metal complexes are shown in the following Scheme 1 for formula (V):

Scheme 1: General examples of metal salts and metal complexes of the imidodiphosphates V.

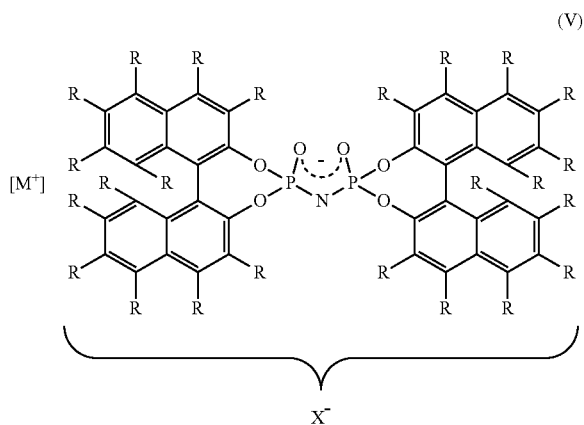

In Scheme 1, any metals or organic cations, e.g. tertiary ammonium ions, can be represented by M. Even though the compounds are shown as salts in scheme 1, the precise structure with metals is not known; they can also have the structure of metal complexes. The formulation metal salts or metal complexes is therefore used for the purposes of the present invention. The metal compounds are not restricted to particular metal compounds or complexes. Suitable metal compounds are derived from Li, Na, K, Rb, Cs, Be, Mg, Ca, Sr, Ba, Sc, Ti, V, Cr, Mn, Fe, Co, Ni, Cu, Zn, Y, Zr, Mo, Ru, Rh, Pd, Ag, W, Re, Os, Ir, Pt, Au, Al, Pb, La, Sm, Eu, Yb, U.

Scheme 2: Examples of possible cations M$^+$X$^-$

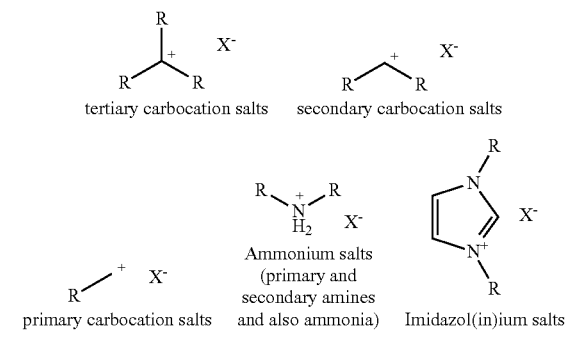

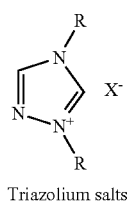
Triazolium salts

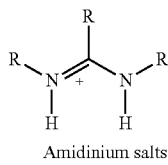
Amidinium salts

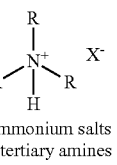
Ammonium salts of tertiary amines

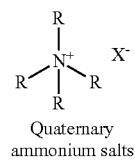
Quaternary ammonium salts

M⁺LₙX⁻
Metal salts

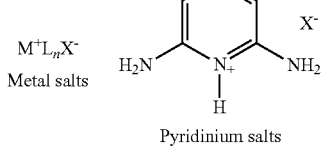
Pyridinium salts

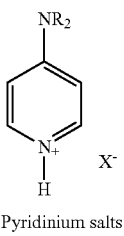
Pyridinium salts

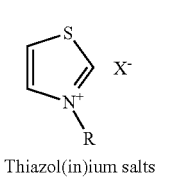
Thiazol(in)ium salts

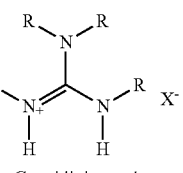
Guanidinium salts

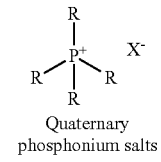
Quaternary phosphonium salts

The imidodiphosphates of the invention and their organic salts, metal salts and metal complexes can be prepared according an exemplary reaction path shown for imido-di-(BINOL-phosphate):

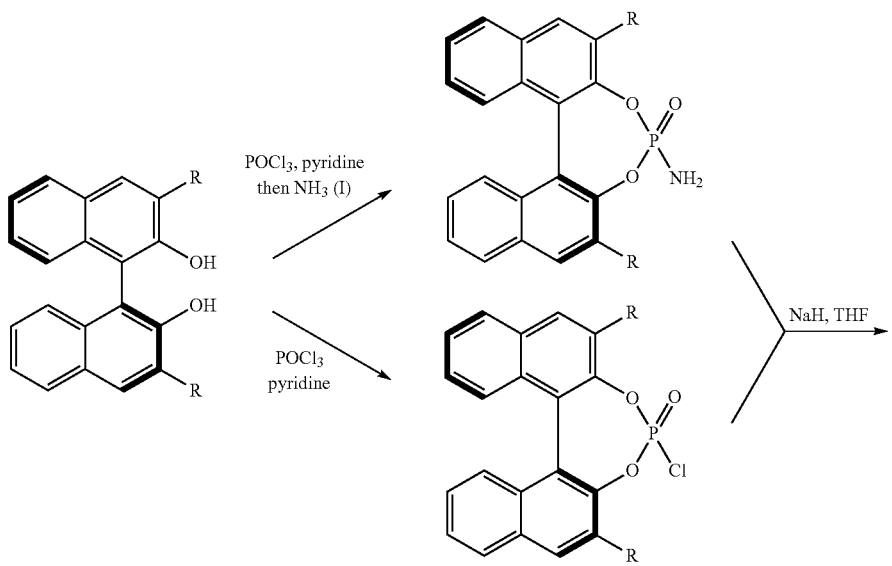

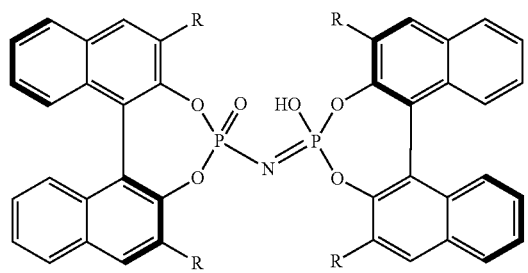

more specifically for the derivative with R=triethylphenyl-:

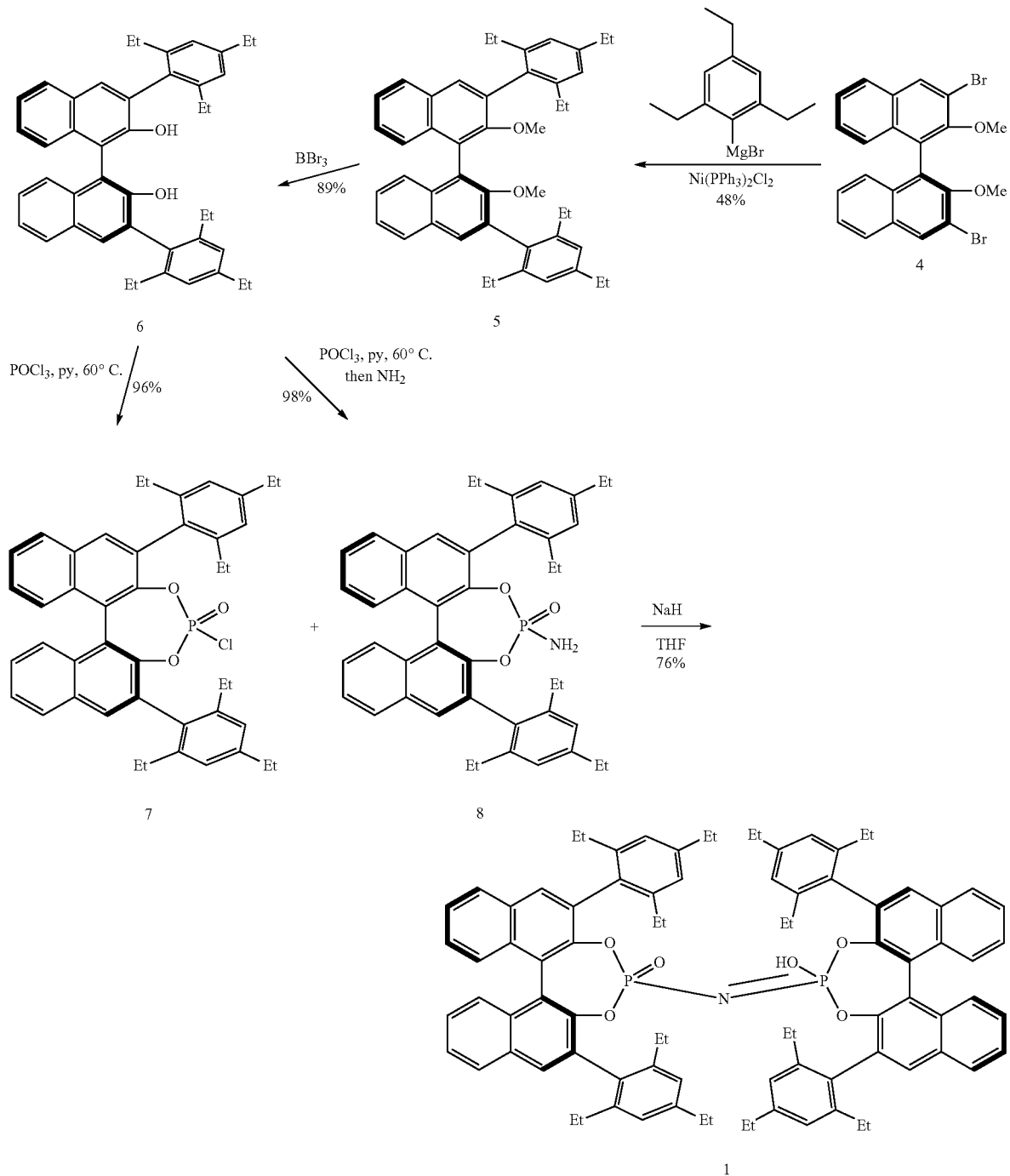

Use as Catalysts

The imidodiphosphates of the invention and their organic salts, metal salts and metal complexes are particularly suitable as strong, chiral Brønsted acid catalysts or chiral Lewis acid catalysts for many reactions, in particular for the activation of ketones, aldehydes, alkenes, imines, enol ethers, ethers, alkynes, and acetals.

The reactions in which compounds according to the invention can be used as catalysts include reactions such as aldol reactions, vinylic aldol reactions, Mukaiyama aldol reactions, vinylic Mukaiyama aldol reactions, Mukaiyama-Michael reactions, Michael additions, Mannich reactions, TMSCN additions onto aldehydes and ketones, esterifications, etherifications, pinacol rearrangements, as well as acetalizations, transacetalization, spiroacetalization and related reactions, cycloadditions, hydroaminations, hydroalkoxylation, hydrations, haloalkoxylation, haloamination, olefin activations in general, Friedel-Crafts reactions, epoxide openings, Ritter reactions, nucleophilic substitutions of alcohols, asymmetric ring openings, asymmetric reductions, transfer hydrogenations, alkyne additions, allylations, propargylations, reductions, epoxidations, olefin metathesis, isomerizations, iminium catalysis and enamine catalysis, as exemplified in the following reaction schemes.

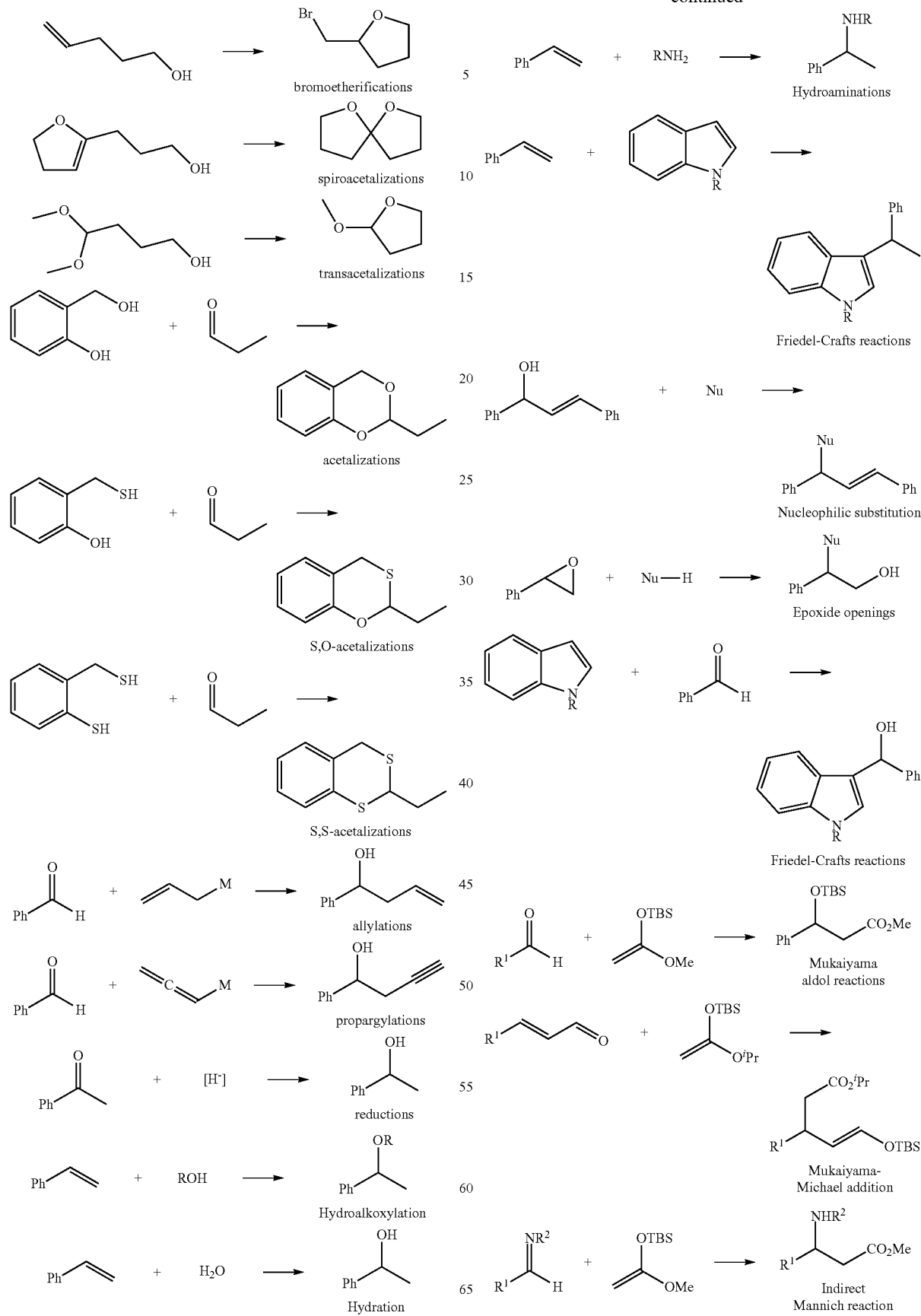

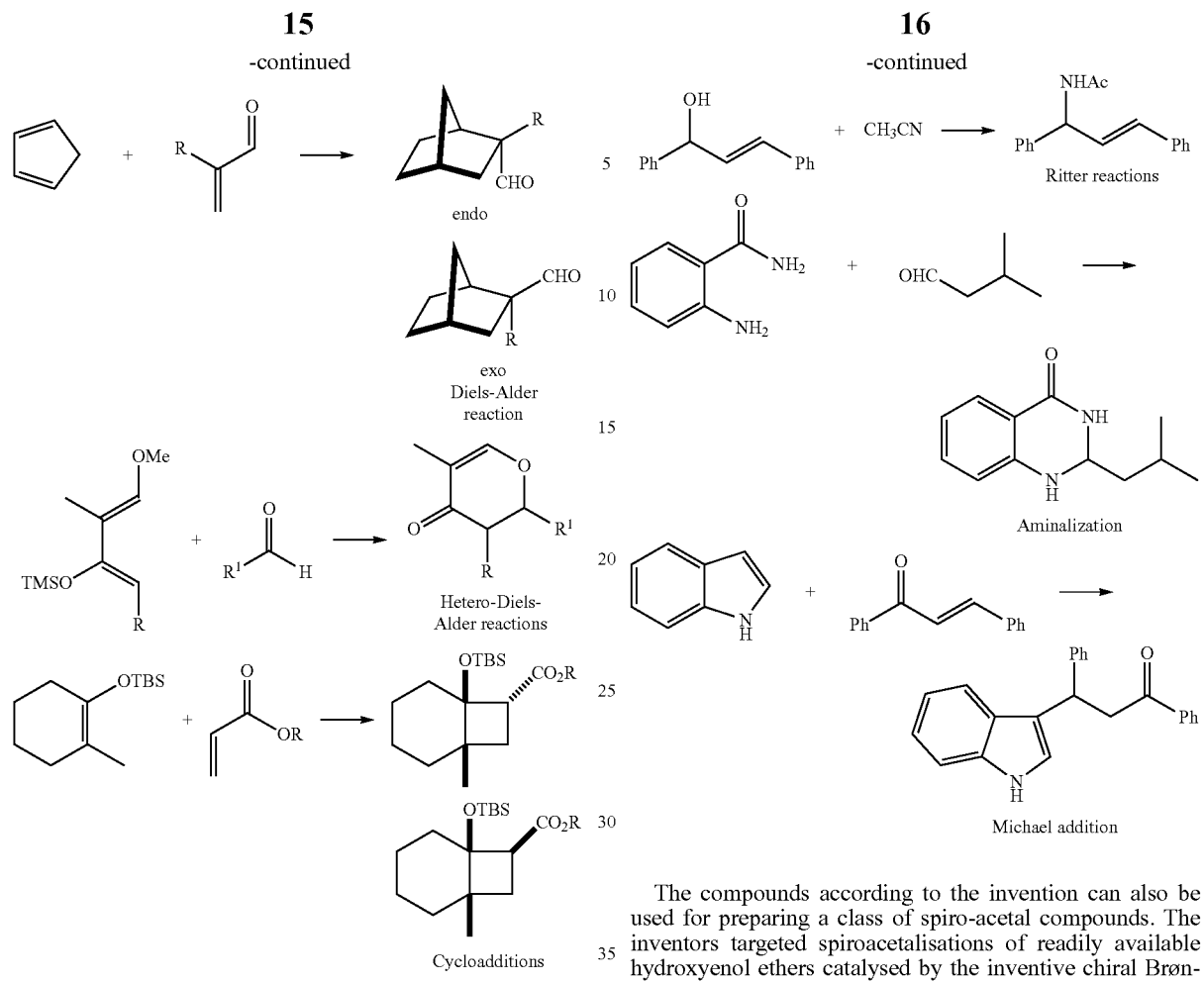
The compounds according to the invention can also be used for preparing a class of spiro-acetal compounds. The inventors targeted spiroacetalisations of readily available hydroxyenol ethers catalysed by the inventive chiral Brønsted acid as shown in the following reaction schemes:
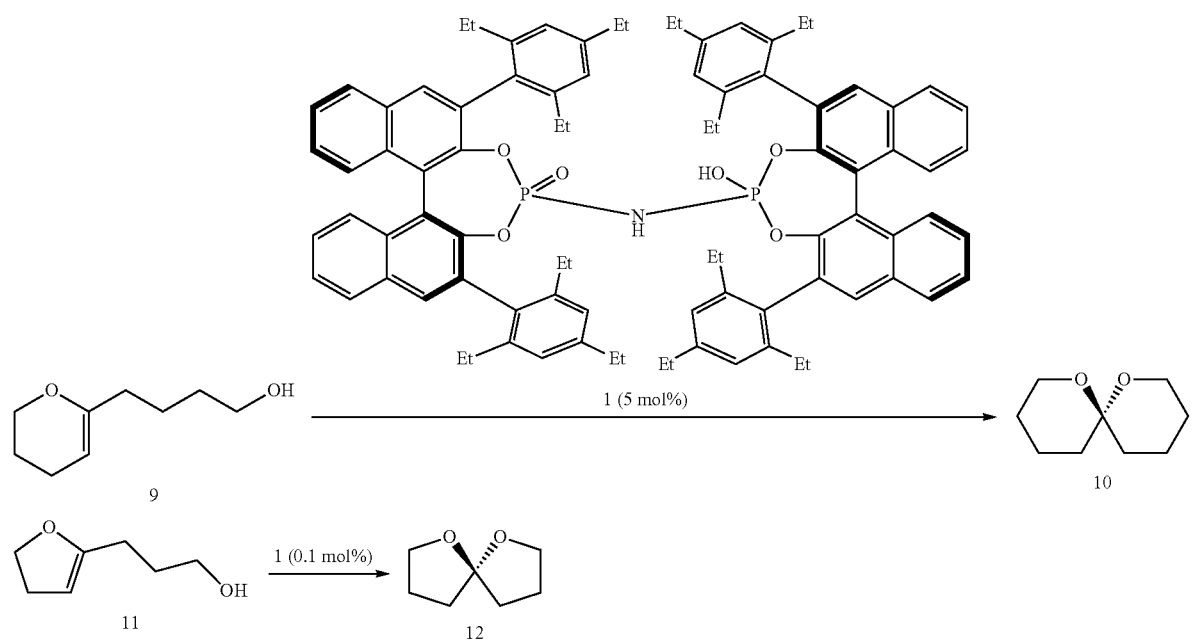

Use of the inventive catalyst 1 lead to the first highly enantioselective catalytic spiroacetalisation reaction to obtain (S)-olean 10 from alcohol 9 with an excellent enantiomeric ratio of 98:2. The (R)-enantiomer of olean was easily obtained by using the enantiomer of the catalyst. Compound 12 was obtained from alcohol 11 under similar conditions also with an excellent enantiomeric ratio of 97:3. Imidodiphosphoric acid catalyst 1 proved quite general and various other small spiroacetals were obtained with high enantioselectivity. Consequently, the present invention is also directed to the use of the inventive compounds for preparing spiro-acetals.

The chiral imidodiphosphates of the general formula (I) can also be used as chiral anions in phase transfer catalysts for phase-transfer catalysis.

As it can be seen from the above, the inventors have designed a novel class of Brønsted acids, in particular employing a $C_2$-symmetric imidodiphosphate anion. In principle, such a $C_2$-symmetric imidodiphosphate moiety has two distinct Brønsted basic sites, O and N. The corresponding acid should have a flexible relative positioning of acid/basic pairs due to free P—N rotation. However, the inventor's catalyst design aimed at restricting the imidodiphosphate moiety to a single O,O-syn conformation preferably between two identical BINOL subunits with bulky 3,3'-substituents. The inventors have found that the inclusion of two BINOL subunits will result in their interlocking due to sterically demanding 3,3'-substituents as shown here:

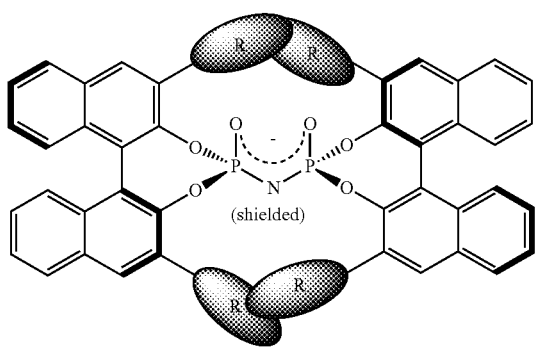

As a direct consequence, the BINOL subunits are unable to freely rotate and the resulting molecular structure possesses a very high rigidity. Importantly, such arrangement also resulted in the sterical blocking of the undesirable alternative Brønsted basic N-site. As the two BINOL subunits are identical, anion is $C_2$-symmetric, and has therefore only a single type of catalytically relevant Brønsted basic site. Consequently, the corresponding Brønsted acid possesses a single catalytically active bifunctional acid/base pair with a fixed geometry. The interlocking of BINOL-subunits could in principle also result in the conformational locking of the imidodiphosphate moiety in the O,O-anti conformation to give the O,O-anti-atropisomer. However, the inventors found out that the formation of the corresponding O,O-anti-atropisomer will be disfavoured with bulky 3,3'-substituents on its backbone due to sterical reasons.

The inventors have thus shown here that Brønsted acids with extreme steric demand and chiral pockets reminiscent of those found in enzymes can overcome limitations and solve an important problem in organic synthesis. According to the invention, the concepts as described open the door for the development of asymmetric reactions which include small and/or loosely bound molecules, and will be widely applicable.

The invention is further illustrated by the following Examples.

EXAMPLES

Catalyst Preparation

Synthesis of imidodiphosphoric acids 1

(S)-2,2'-Dimethoxy-3,3'-bis(2,4,6-triethylphenyl)-1,1'-binaphthalene (5)

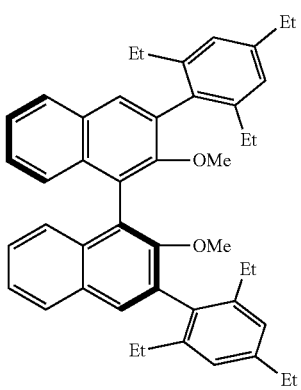

To magnesium turnings (583 mg, 24 mmol) activated with 1,2-dibromoethane in diethyl ether (4 ml), 2-bromo-1,3,5-triethylbenzene (3.86 g, 16 mmol) and diethylether (20 ml) were added alternately during 30 min. After complete addition the mixture was refluxed (oil bath heating) for 21 h. After cooling to ambient temperature, the solution was added to a mixture of (S)-3,3'-dibromo-2,2'-dimethoxy-1,1'-binaphthalene (4, 1.89 g, 4.0 mmol) and Ni(PPh$_3$)$_2$Cl$_2$ (393 mg, 0.60 mmol) in anhydrous diethyl ether (40 ml). The reaction mixture was refluxed for 28 h, cooled to ambient temperature, carefully treated with saturated aqueous NH$_4$Cl solution (40 ml) and water (40 ml), and extracted with CH$_2$Cl$_2$ (100 ml, 50 ml). The combined organic layers were dried (MgSO$_4$), filtered, and the solvent removed under reduced pressure. The residue was purified by column chromatography on silica gel using 10-15% CH$_2$Cl$_2$/hexane as the eluent yielding the title compound as a colorless solid (1.22 g, 48%).

$^1$H-NMR (400 MHz, CD$_2$Cl$_2$): δ 7.89 (d, J=8.1 Hz, 2H), 7.74 (s, 2H), 7.44-7.40 (m, 2H), 7.32-7.25 (m, 4H), 7.06 (s, 2H), 7.05 (m, 2H), 3.10 (s, 6H), 2.70 (q, J=7.6 Hz, 4H), 2.51 (q, J=7.6 Hz, 4H), 2.46 (q, J=7.6 Hz, 4H), 1.30 (t, J=7.6 Hz, 6H), 1.15 (t, J=7.6 Hz, 6H), 1.08 (t, J=7.6 Hz, 6H); $^{13}$C-NMR (100 MHz, CD$_2$Cl$_2$): δ 155.0, 144.0, 142.9, 142.8, 134.9, 134.4, 134.2, 131.4, 130.8, 128.3, 126.4, 125.9, 125.4 (2C), 125.3, 125.0, 60.1, 29.1, 27.4, 27.3, 15.8, 15.6, 15.4; HRMS (ESI+) (m/z): [M+Na] calcd for C$_{46}$H$_{50}$O$_2$Na, 657.3703; found, 657.3708.

(S)-3,3'-bis(2,4,6-triethylphenyl)-[1,1'-binaphthalene]-2,2'-diol (6)

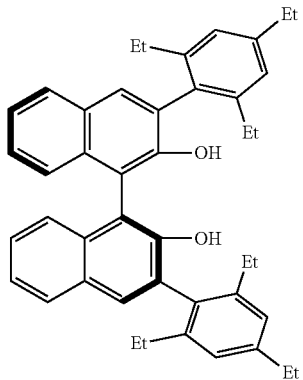

A 1 M solution of BBr₃ in CH₂Cl₂ (7.56 ml, 7.56 mmol) was added dropwise to the solution of (S)-5 (1.20 g, 1.89 mmol) in CH₂Cl₂ (20 ml) at 0° C. under argon. After 40 h at room temperature, the solution was cooled to 0° C., water (50 ml) was carefully added, and the mixture was extracted with CH₂Cl₂ (50 ml). The organic layer was washed with saturated aqueous Na₂CO₃ solution (50 ml), dried (MgSO₄), filtered, and the solvent was removed under reduced pressure. The residue was purified by column chromatography on silica gel using 20% CH₂Cl₂/hexane as the eluent yielding the title compound as a colorless solid (1.02 g, 89%).

$^1$H-NMR (400 MHz, CD₂Cl₂): δ 7.91 (d, J=7.9 Hz, 2H), 7.78 (s, 2H), 7.41-7.37 (m, 2H), 7.35-7.31 (m, 2H), 7.24-7.22 (m, 4H), 7.09-7.07 (m, 4H), 5.06 (s, 2H), 2.70 (q, J=7.6 Hz, 4H), 2.57-2.31 (m, 8H), 1.30 (t, J=7.7 Hz, 6H), 1.10 (t, J=7.6 Hz, 6H), 1.02 (t, J=7.6 Hz, 6H); $^{13}$C-NMR (100 MHz, CD₂Cl₂): δ 150.9, 145.0, 143.9, 143.8, 133.9, 132.2, 131.5, 129.6, 129.4, 128.7, 127.1, 126.2, 124.6, 124.2, 113.5, 29.1, 27.37, 27.36, 15.7, 15.6, 15.5 (+1 aromatic C, overlapped); HRMS (ESI+) (m/z): [M+Na] calcd for C₄₄H₄₆O₂Na, 629.3390; found, 629.3387.

(S)-4-chloro-2,6-bis(2,4,6-triethylphenyl)dinaphtho[2,1-d:1',2'-f][1,3,2]dioxaphosphepine 4-oxide (7)

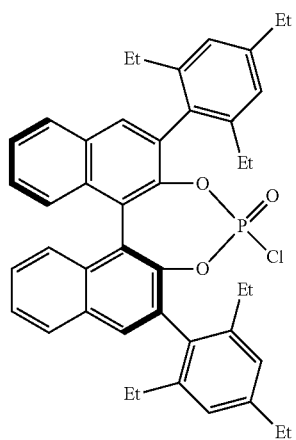

To a solution of (S)-6 (553 mg, 0.912 mmol) in pyridine (3 ml) under argon was added POCl₃ (255 μl, 420 mg, 2.74 mmol) at room temperature. The mixture was stirred at 60° C. for 1.5 h and then concentrated to dryness under vacuum. The residue was passed through a short silica gel column (10 g) using CH₂Cl₂ as the eluent yielding the title compound as a colorless solid (604 mg, 96%).

$^1$H-NMR (400 MHz, CD₂Cl₂): δ 8.01-7.98 (m, 2H), 7.96 (s, 1H), 7.92 (s, 1H), 7.59-7.54 (m, 2H), 7.38-7.30 (m, 4H), 7.11-7.12 (m, 2H, two overlapped doublets with small J), 7.05 (d, J=1.2 Hz, 1H), 7.02 (d, J=1.2 Hz, 1H), 2.74-2.69 (m, 4H), 2.55-2.29 (m, 8H), 1.32 (t, J=7.6 Hz, 3H, overlapped), 1.31 (t, J=7.6 Hz, 3H, overlapped), 1.26 (t, J=7.5 Hz, 3H), 1.18 (t, J=7.6 Hz, 3H), 1.01 (t, J=7.5 Hz, 3H, overlapped), 0.99 (t, J=7.5 Hz, 3H, overlapped); $^{13}$C-NMR (100 MHz, CD₂Cl₂): δ 145.3 (d, $J_{C-P}$=11.1 Hz), 145.2 (d, $J_{C-P}$=9.1 Hz), 144.9, 144.6, 143.6, 143.3, 142.9, 142.8, 133.4, 132.53, 132.49, 132.46, 132.44, 132.2, 132.0, 131.91, 131.90, 131.79, 131.77, 131.73, 128.8, 127.5, 127.3, 127.2, 126.8, 125.9, 125.5, 125.4, 125.0, 122.54 (d, $J_{C-P}$=2.5 Hz), 122.48 (d, $J_{C-P}$=2.8 Hz), 29.14, 19.12, 27.8, 27.3, 27.18, 27.15, 16.3, 15.57, 15.55, 15.49, 15.1, 14.9 (including additional peaks due to unassigned $^{13}$C—$^{31}$P-coupling, some signals are overlapped); $^{31}$P-NMR (162 MHz, CD₂Cl₂): δ 8.26 (s); HRMS (ESI+) (m/z): [M+Na] calcd for C₄₄H₄₄O₃ClPNa, 709.2609; found, 709.2606.

(S)-4-amino-2,6-bis(2,4,6-triethylphenyl)dinaphtho[2,1-d:1',2'-f][1,3,2]dioxaphosphepine 4-oxide (8)

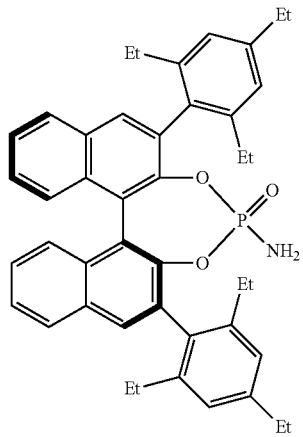

To a solution of (S)-6 (464 mg, 0.764 mmol) in pyridine (3 ml) under argon was added POCl₃ (214 μl, 351 mg, 2.29 mmol) at room temperature. After 1.5 h at 60° C., the mixture was cooled to −78° C. and anhydrous ammonia gas was condensed into the reaction flask (ca. 10 ml). The cooling bath was removed and the mixture was allowed to warm to room temperature. The reaction mixture was then concentrated to dryness under vacuum. Residue was passed through short silica gel column (10 g) using CH₂Cl₂ as the eluent yielding the title compound as a colorless solid (500 mg, 98%).

$^1$H-NMR (400 MHz, CD₂Cl₂): δ 7.99-7.94 (m, 2H), 7.91 (s, 1H), 7.84 (s, 1H), 7.55-7.50 (m, 2H), 7.37-7.31 (m, 4H), 7.10 (d, J=1.5 Hz, 1H), 7.08 (d, J=1.4 Hz, 1H), 7.05 (d, J=1.5 Hz, 1H), 6.99 (d, J=1.4 Hz, 1H), 2.74-2.63 (m, 6H), 2.58-2.28 (m, 8H), 1.31 (t, J=7.6 Hz, 3H, overlapped), 1.28 (t, J=7.6 Hz, 3H, overlapped), 1.25 (t, J=7.6 Hz, 3H, overlapped), 1.17 (t, J=7.6 Hz, 3H), 1.00 (t, J=7.5 Hz, 3H, overlapped), 0.99 (t, J=7.5 Hz, 3H, overlapped); $^{13}$C-NMR (100 MHz, CD$_2$Cl$_2$): δ 145.9 (d, J$_{C-P}$=10.7 Hz), 145.2 (d, J$_{C-P}$=8.1 Hz), 144.7, 144.2, 143.8, 143.6, 142.8, 142.1, 133.1, 132.88, 132.85, 132.68, 132.64, 132.61, 132.5, 132.41, 132.38, 131.7, 131.6, 128.7, 128.6, 127.4, 127.3, 126.8, 126.7, 126.2, 126.1, 125.8, 125.6, 125.3, 124.8, 122.8 (d, J$_{C-P}$=2.0 Hz), 122.5 (d, J$_{C-P}$=2.0 Hz), 29.1 (2C), 27.8, 27.3, 27.21, 27.17, 16.5, 15.53, 15.51, 15.4, 15.2, 14.9 (including additional peaks due to unassigned $^{13}$C—$^{31}$P-coupling, some signals are overlapped); $^{31}$P-NMR (162 MHz, CD$_2$Cl$_2$): δ 13.20 (s); HRMS (ESI+) (m/z): [M+Na] calcd for C$_{44}$H$_{46}$NO$_3$PNa, 690.3108; found, 690.3114.

O,O-syn-Imidodiphosphoric acid 1

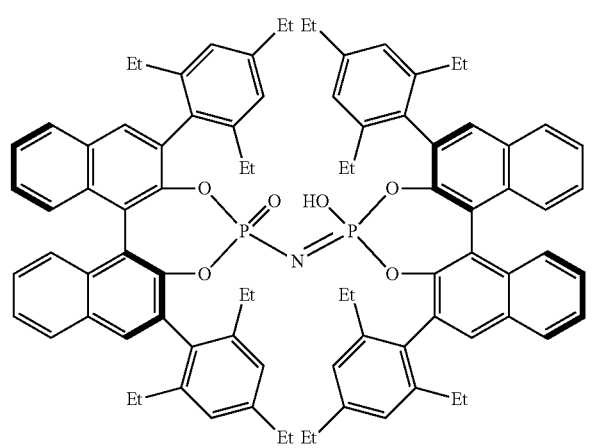

Sodium hydride (60% dispersion of in mineral oil, 84 mg, 2.1 mmol) was added to a solution of (S)-8 (464 mg, 0.764 mmol) and (S)-7 (577 mg, 0.84 mmol) in THF (5 ml) under argon at room temperature. After 14 h at room temperature, 10% aqueous HCl solution (10 ml) and DCM (10 ml) were added, and the mixture was stirred for 1 h. The organic layer was separated and the solvent was removed under reduced pressure. The residue was purified by column chromatography on aluminum oxide (activity I) using 20-100% CH$_2$Cl$_2$/hexane followed by 2-8% EtOAc/DCM as the eluents giving a colorless solid. The solid was dissolved in CH$_2$Cl$_2$ (10 ml) and stirred with 3N aqueous HCl (10 ml) for 4 h. The organic layer was separated, washed with 3N aqueous HCl (10 ml) and concentrated under reduced pressure to give the title compound as a colorless solid (695 mg, 76%).

$^1$H-NMR (500 MHz, CD$_2$Cl$_2$): δ 7.90 (d, J=8.2 Hz, 1H), 7.87 (d, J=8.2 Hz, 1H), 7.79 (s, 1H), 7.59 (s, 1H), 7.51 (t, J=7.5 Hz, 1H), 7.46-7.38 (m, 3H), 7.23-7.20 (m, 1H), 7.05 (d, J=8.6 Hz, 1H), 6.97 (s, 1H), 6.863 (s, 1H), 6.856 (s, 1H), 6.61 (broad s, 1.8H, acidic H+H$_2$O), 6.39 (s, 1H), 2.65-2.50 (m, 4H), 2.32-2.12 (m, 5H), 2.07-2.00 (m, 1H), 1.92-1.82 (m, 1H), 1.20 (t, J=7.6 Hz, 3H, overlapped), 1.19 (t, J=7.6 Hz, 3H, overlapped), 1.17-1.10 (m, 1H, overlapped), 1.08 (t, J=7.5 Hz, 3H), 0.95 (t, J=7.5 Hz, 3H), 0.82 (t, J=7.5 Hz, 3H), 0.04 (t, J=7.5 Hz, 3H); $^{13}$C-NMR (125 MHz, CD$_2$Cl$_2$): δ 146.4, 145.8, 144.2, 144.0, 143.8, 143.5, 143.4, 142.5, 133.1, 133.0, 132.94, 132.86, 132.82, 132.5, 132.4, 132.1, 131.6, 131.3, 128.6, 128.5, 127.1, 126.5, 126.4, 125.9, 125.7, 125.6, 125.4, 124.72, 124.70, 122.7, 122.2, 29.0, 28.9, 27.28, 27.25, 26.99, 26.97, 15.85 (2C), 15.77, 15.3, 15.2, 14.9; $^{31}$P-NMR (202 MHz, CD$_2$Cl$_2$): δ 4.94 (s);

HRMS (ESI−) (m/z): [M-H] calcd for C$_{88}$H$_{88}$NO$_6$P$_2$, 1316.6092; found, 1316.6096.

O,O-syn-Imidodiphosphoric acid 2

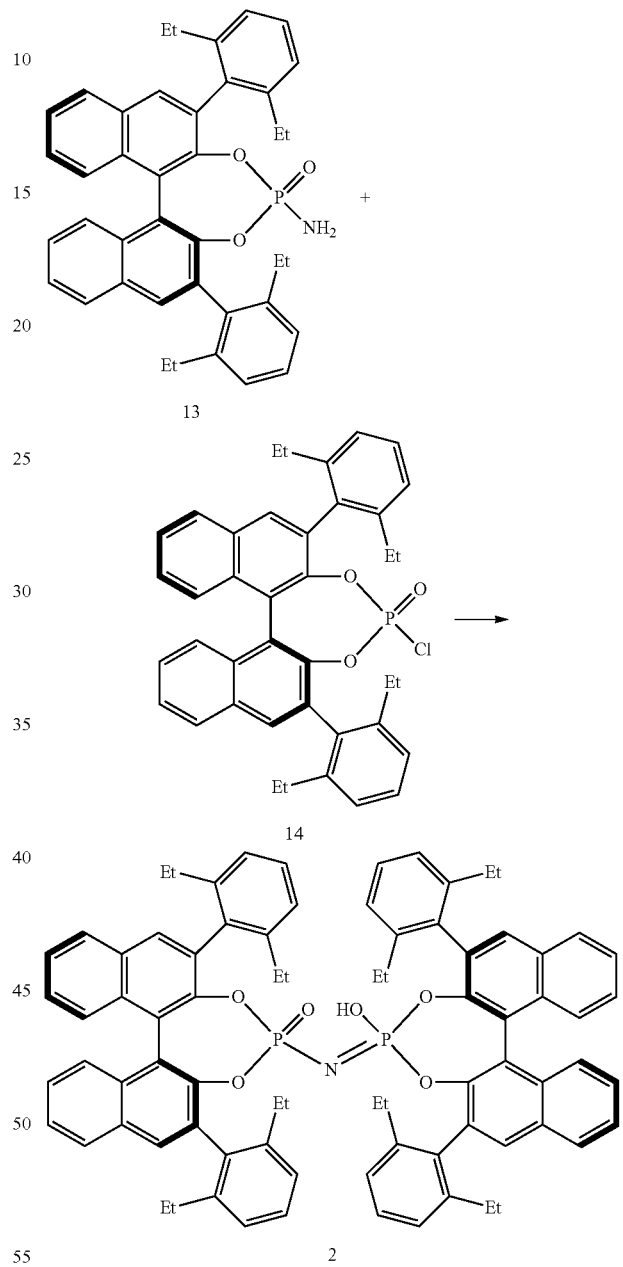

Sodium hydride (60% dispersion of in mineral oil, 13.7 mg, 0.34 mmol) was added to a solution of (S)-13 (70 mg, 0.114 mmol) and (S)-14 (114 mg, 0.18 mmol) in THF (2 ml) under argon at room temperature. After 2.5 days at room temperature 10% aqueous HCl solution (5 ml) and DCM (5 ml) were added to the mixture, which was stirred for 4 h. The organic layer was separated and the solvent removed under reduced pressure. The residue was purified by column chromatography on aluminum oxide (activity I) using 0-12% EtOAc/DCM as the eluent giving a colorless solid.

The solid was dissolved in CH$_2$Cl$_2$ (5 ml) and stirred with 3N aqueous HCl (10 ml) for 4 h. The organic layer was separated, and concentrated under reduced pressure to give the title compound as a colorless solid (76 mg, 61%).

$^1$H-NMR (500 MHz, acetone-d$_6$): δ 8.05 (d, J=8.2 Hz, 2H), 8.02 (d, J=8.2 Hz, 2H), 7.89 (s, 2H), 7.69 (s, 2H), 7.55 (t, J=7.5 Hz, 2H), 7.50 (t, J=7.5 Hz, 2H), 7.45 (t, J=7.6 Hz, 2H), 7.40 (d, J=8.7 Hz, 2H), 7.28 (t, J=7.7 Hz, 2H), 7.18 (t, J=7.6 Hz, 2H), 7.11 (t, J=7.6 Hz, 2H), 7.07 (d, J=8.6 Hz, 2H), 7.04 (d, J=7.6 Hz, 2H), 7.00 (d, J=7.4 Hz, 2H), 6.93 (d, J=7.4 Hz, 2H), 6.65 (d, J=7.6 Hz, 2H), 2.33-2.07 (m, 12H), 1.96-1.89 (m, 2H), 1.37-1.31 (m, 2H), 1.05 (t, J=7.7 Hz, 6H), 1.03 (t, J=7.7 Hz, 6H), 0.79 (t, J=7.5 Hz, 6H), 0.01 (t, J=7.5 Hz, 6H); $^{13}$C-NMR (125 MHz, acetone-d$_6$): δ 146.7, 146.4, 144.0, 143.6, 143.3, 142.7, 136.1, 136.0, 133.5, 133.1, 133.0, 132.8, 132.5, 132.0, 131.7, 129.2, 129.1, 128.6, 128.5, 127.5, 127.3, 127.1, 127.1, 126.8, 126.5, 126.4, 125.9, 125.5, 125.3, 123.2, 122.8, 28.0, 27.7, 27.4, 27.3, 15.8, 15.4, 15.3, 14.9; $^{31}$P-NMR (202 MHz, acetone-d$_6$): δ 5.73 (s); HRMS (ESI−) (m/z): [M−H] calcd for C$_{80}$H$_{72}$NO$_6$P$_2$, 1204.4840; found, 1204.4846.

O,O-syn-Imidodiphosphoric acid 3

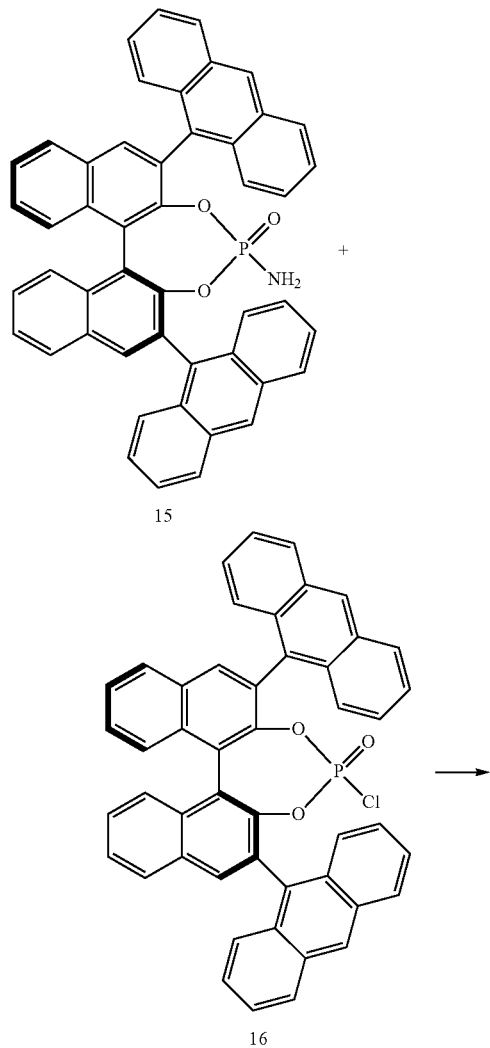

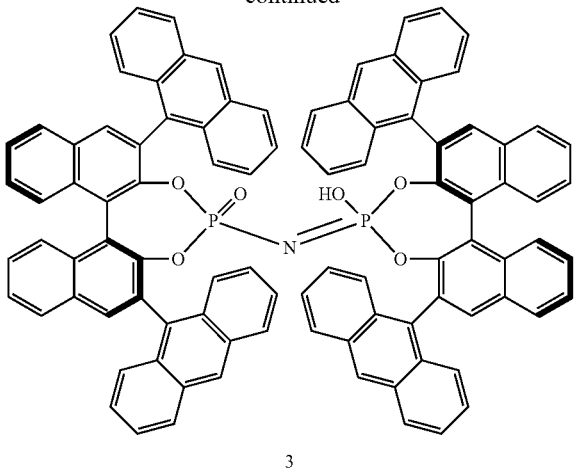

3

Sodium hydride (60% dispersion of in mineral oil, 24 mg, 0.60 mmol) was added to a solution of (S)-15 (140 mg, 0.20 mmol) and (S)-16 (173 mg, 0.24 mmol) in THF (2 ml) under argon at room temperature. After 4 days at room temperature, water (5 ml) was added and the mixture was extracted with CH$_2$Cl$_2$ (5×10 ml). The organic extracts were washed with brine, dried (MgSO$_4$), filtered, and the solvent was removed under reduced pressure. The residue was purified by column chromatography on silica gel using 0-4% EtOAc/DCM as the eluent giving a colorless solid. The solid was dissolved in CH$_2$Cl$_2$ (10 ml) and washed with 3 N aqueous HCl (10 ml). The organic layer was separated, and concentrated under reduced pressure to give the title compound as a yellowish solid (101 mg, 37%).

$^1$H-NMR (500 MHz, CD$_2$Cl$_2$): δ 8.21 (s, 2H), 8.06 (d, J=8.4 Hz, 4H), 7.91 (s, 2H), 7.87 (d, J=8.2 Hz, 2H), 7.83 (d, J=8.6 Hz, 2H), 7.80 (s, 2H), 7.74-7.64 (m, 14H), 7.53 (t, J=7.6 Hz, 2H), 7.48-7.39 (m, 8H), 7.36-7.33 (m, 2H), 7.31-7.27 (m, 6H), 7.11-7.10 (m, 4H), 6.91-6.87 (m, 2H), 5.87 (t, J=7.4 Hz, 2H), 5.59-5.56 (m, 2H), 5.15 (broad s, 2.43H, acidic H+H$_2$O); $^{13}$C-NMR (125 MHz, CD$_2$Cl$_2$): δ 146.5, 146.4, 146.4, 146.1, 146.1, 146.0, 133.9, 133.1, 133.0, 132.8, 131.9, 131.4, 131.2, 131.1, 131.0, 131.0, 130.8, 130.7, 130.4, 130.3, 130.2, 130.2, 130.0, 129.0, 129.0, 128.8, 128.7, 128.5, 128.1, 127.5, 127.4, 127.3, 127.2, 127.1, 127.1, 126.8, 126.6, 126.2, 126.1, 125.5, 125.4, 125.2, 125.1, 124.4, 124.2, 124.0, 124.0, 122.5; $^{31}$P-NMR (202 MHz, CD$_2$Cl$_2$): δ 13.74 (s); HRMS (ESI−) (m/z): [M−H] calcd for C$_{96}$H$_{56}$NO$_6$P$_2$, 1380.3588; found, 1380.3584.

Substrate Preparation 4-(3,4-Dihydro-2H-pyran-6-yl)butan-1-ol (9)

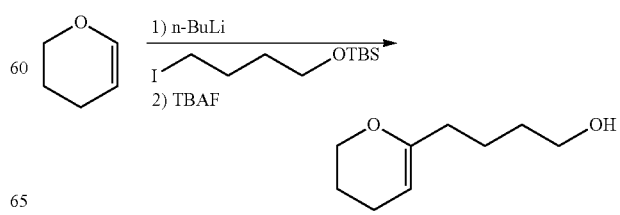

A 2.5 M solution of n-butyl lithium in hexane (2 ml, 5 mmol) was added dropwise to a solution of 3,4-dihydro-2H-pyran (457 µl, 420 mg, 5 mmol) in THF (2 ml) at 0° C. under argon atmosphere. After being stirred at 50° C. for 1 h, the mixture was cooled to −10° C. A solution of the tert-butyl(4-iodobutoxy)dimethylsilane (5 mmol) in THF (2 ml) was added to the mixture at −10° C. The mixture was heated to 50° C. for 1.5 h, cooled to room temperature, and filtered through celite and aluminum oxide (5 g, activity III) using hexane as the eluent. The solvent was removed under reduced pressure and the residue was treated with 1 M solution of tetrabutylammonium fluoride (6 mmol, 6 ml) for 1 h 45 min. The mixture was then diluted with hexane (10 ml) and filtered through celite and aluminum oxide (5 g, activity III) using Et$_2$O as the eluent. The solvent was removed under reduced pressure and the residue was purified by column chromatography on aluminum oxide (activity III) using 10% EtOAc/hexane as the eluent giving a colorless oil, 349 mg, 45%.

mixture was filtered through aluminum oxide (10 g, activity III, preconditioned with Et$_2$O) using 5% MeOH/Et$_2$O as eluent. The solvent was removed under reduced pressure and the residue was purified by column chromatography on aluminum oxide (activity III) using 20% EtOAc/hexane as the eluent giving a colorless oil, 483 mg, 97%.

$^1$H-NMR (400 MHz, DMSO-d$_6$): δ 4.59-4.57 (m, 1H), 4.39 (t, J=5.2 Hz, 1H), 4.20 (t, J=9.4 Hz, 2H), 3.38 (q, J=6.0 Hz, 2H), 2.54-2.49 (m, 2H, overlap with solvent), 2.07-2.03 (m, 2H), 1.59-1.52 (m, 2H); $^{13}$C-NMR (100 MHz, DMSO-d$_6$): δ 158.2, 93.3, 69.0, 60.1, 29.6, 29.4, 23.9; HRMS (EI (FE)) (m/z): [M] calcd for C$_7$H$_{12}$O$_2$, 128.0837; found, 128.0836.

Catalytic Tests

General Procedure for the Catalytic Asymmetric Spiroacetalisation

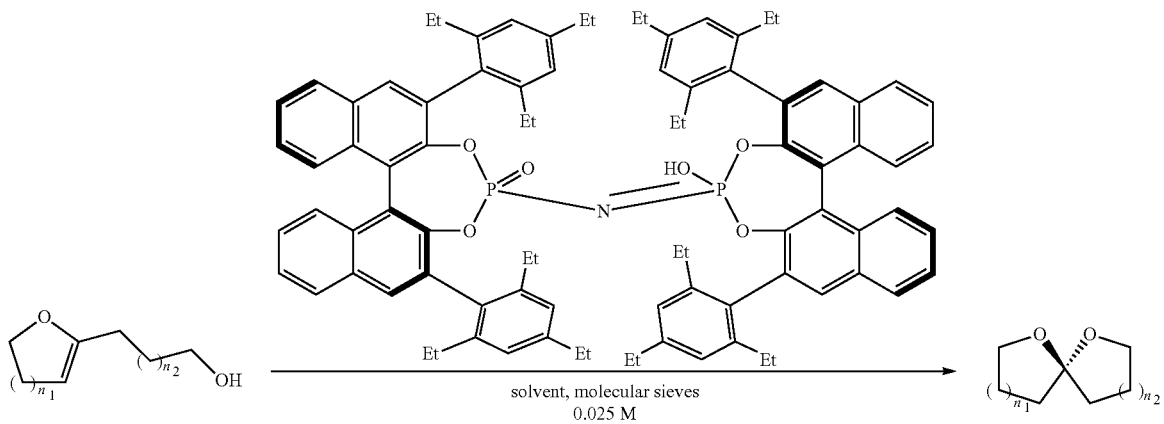

$^1$H-NMR (500 MHz, C$_6$D$_6$): δ 4.45 (t, J=3.7 Hz, 1H), 3.77-3.75 (m, 2H), 3.37-3.34 (m, 2H), 2.06 (t, J=7.5 Hz, 2H), 1.83-1.80 (m, 2H), 1.60-1.54 (m, 2H), 1.49-1.45 (m, 2H), 1.44-1.39 (m, 2H), 0.69 (t, J=5.2 Hz, 1H); $^{13}$C-NMR (125 MHz, C$_6$D$_6$): δ 154.8, 95.3, 66.0, 62.6, 34.6, 32.6, 23.7, 22.8, 20.6; HRMS (EI (FE)) (m/z): [M] calcd for C$_9$H$_{16}$O$_2$, 156.1150. found, 156.1149.

3-(4,5-Dihydrofuran-2-yl)propan-1-ol (11)

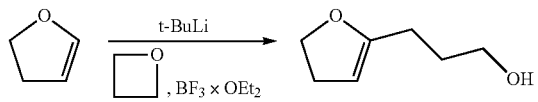

A 1.7 M solution of tert-butyl lithium in pentane (2.94 ml, 5 mmol) was added dropwise to a solution of dihydrofuran (378 µl, 350 mg, 5 mmol) in THF (2 ml) at −78° C. under argon atmosphere. After being stirred at 0° C. for 30 min, the mixture was cooled to −78° C. and diluted with THF (3 ml). Oxetane (650 µl, 581 mg, 10 mmol) was added to this mixture followed by the dropwise addition of BF$_3$.OEt$_2$ (634 µl, 710 mg, 5 mmol). The mixture was stirred for 15 min at −78° C., and Et$_3$N (2 ml) was added dropwise and the mixture was allowed to warm to room temperature. The Solvent (7 ml) and molecular sieves were cooled to the reaction temperature in a vial closed with a septum. A solution of substrate (0.25 mmol) in solvent (2 ml) was added, and the mixture stirred for 5-10 min allowing it to reach the reaction temperature. To the mixture a solution of catalyst 1 in solvent (1 ml) was added dropwise. After 12-24 h at the designated temperature the reaction was quenched with Et$_3$N (50 µl).

Purification was performed by chromatography as described for individual case. Solutions of products after chromatography were carefully concentrated to ca. <0.1 ml, and immediately dissolved in C$_6$D$_6$ (3 ml). Yield was determined by $^1$H NMR analysis using 1 ml of this solution and Ph$_3$CH (20.4 mg, 0.0833 mmol) as internal standard, integration of Ph$_3$CH vs. product —CH$_2$O—. NMR spectra without remaining solvent are obtained after concentrating the other 2 ml of the C$_6$D$_6$ solution (previously used for optical rotation measurement) to <0.3 ml and diluting with C$_6$D$_6$. Alternatively, after concentration to <50 mg, part of the sample was directly used for optical rotation measurement, and the rest immediately used for NMR analysis, and yield corrected for residual solvent by integration in $^1$H NMR spectrum. Due to the volatility of the products some imprecision in the determination of yields and optical rotation values is expected.

Absolute configuration of (S)-10 was determined by comparison with literature value and configurations of other products were assigned by analogy.

S)-1,7-Dioxaspiro[5.5]undecane ((S)-10

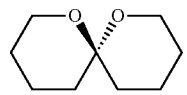

Reaction conditions: catalyst loading, 5 mol %; solvent, tert-butyl-methyl ether; molecular sieves, 4 Å (50 mg); temperature, −25° C., 24 h. Purification: mixture concentrated to <1 ml, silica gel column using 5% Et$_2$O/pentane as eluent. Colorless liquid, yield 77%.

$^1$H-NMR (400 MHz, C$_6$D$_6$): δ 3.71-3.64 (m, 2H), 3.57-3.52 (m, 2H), 2.03-1.91 (m, 2H), 1.68-1.62 (m, 2H), 1.51-1.30 (m, 6H), 1.27-1.22 (m, 2H); $^{13}$C-NMR (100 MHz, C$_6$D$_6$): δ 94.9, 60.2, 36.3, 25.8, 19.1; HRMS (EI (FE)) (m/z): [M] calcd for C$_9$H$_{16}$O$_2$, 156.1150. found, 156.1151; [α]$_D^{25}$=+121.5° (c=0.85 in pentane, er 98:2) (Literature value for (R)-10: [α]$_D^{19}$=−122.8°, c=3.2 in pentane, e.r. >97.5:2.5); Chiral GC (Column: 25 m Lipodex-G (octakis-(2,3-di-O-pentyl-6-O-methyl)-γ-cyclodextrin), i.D. 0.25 mm; Detector: FID; Temperature: injector 230° C., detector 350° C., oven 100° C.; gas: 0.5 bar H$_2$), t$_{minor}$=4.86 min, t$_{major}$=5.36 min, er=98:2.

R)-1,7-Dioxaspiro[5.5]undecane ((R)-10

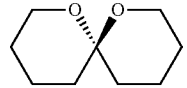

Reaction conditions: catalyst loading, 5 mol %; solvent, tert-butyl-methyl ether; molecular sieves, 4 Å (50 mg); temperature, −25° C., 12 h. Purification: mixture concentrated to <1 ml, silica gel column using 5% Et$_2$O/pentane as eluent. Colorless liquid, yield 70%.

$^1$H-NMR (500 MHz, C$_6$D$_6$): δ 3.70-3.65 (m, 2H), 3.57-3.53 (m, 2H), 2.02-1.92 (m, 2H), 1.67-1.63 (m, 2H), 1.50-1.30 (m, 6H), 1.27-1.22 (m, 2H); $^{13}$C-NMR (125 MHz, C$_6$D$_6$): δ 94.9, 60.2, 36.3, 25.8, 19.1; [α]$_D^{25}$=−96.3° (c=0.91 in C$_6$D$_6$, er 97.5:2.5); Chiral GC (Column: 25 m Lipodex-G (octakis-(2,3-di-O-pentyl-6-O-methyl)-γ-cyclodextrin), i.D. 0.25 mm; Detector: FID; Temperature: injector 230° C., detector 350° C.; oven 100° C.; gas: 0.5 bar H$_2$), t$_{major}$=4.53 min, t$_{minor}$=5.05 min, er=97.5:2.5.

(S)-1,6-dioxaspiro[4.4]nonane (12)

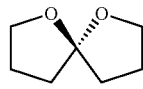

Reaction conditions: catalyst loading, 0.1 mol %; solvent, CH$_2$Cl$_2$; molecular sieves, 3 Å (125 mg); temperature, −55° C., 12 h. Purification: To the mixture Et$_3$N (0.5 ml) was added, mixture concentrated to <1 ml, silica gel column using 10% Et$_2$O/pentane as eluent. Colorless liquid, yield 62%.

$^1$H-NMR (400 MHz, C$_6$D$_6$): δ 3.93-3.87 (m, 2H), 3.74-3.68 (m, 2H), 2.01-1.83 (m, 4H), 1.69-1.61 (m, 2H), 1.58-1.48 (m, 2H); $^{13}$C-NMR (100 MHz, C$_6$D$_6$): δ 114.6, 66.9, 34.8, 25.0; HRMS (EI (FE)) (m/z): [M] calcd for C$_7$H$_{12}$O$_2$, 128.0837; found, 128.0838; [α]$_D^{25}$=+182.4° (c=0.44 in pentane, er 96:4); Chiral GC (Column: 25 m Lipodex-G (octakis-(2,3-di-O-pentyl-6-O-methyl)-γ-cyclodextrin), i.D. 0.25 mm; Detector: FID; Temperature: injector 230° C., detector 350° C., oven 95° C.; gas: 0.5 bar H$_2$), t$_{minor}$=2.82 min, t$_{major}$=3.00 min, er=96:4.

The invention claimed is:

1. A chiral imidodiphosphate having the formula (I):

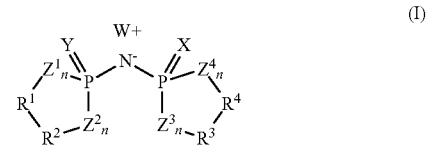

wherein:
X and Y are, independently from each other, the same or different and represent one of O, S, Se and NR$^N$,
Z$^1$ to Z$^4$ represent O,
n stands for 0 or 1,
W is a substituent capable of forming an ionic bond with the imidodiphosphate moiety,
R$^1$ to R$^4$ are, independently from each other, the same or different and are each an aliphatic, heteroaliphatic, aromatic or heteroaromatic group, each optionally being further substituted by one or more heterosubstituents, aliphatic, heteroaliphatic, aromatic or heteroaromatic groups whereby R$^1$ and R$^2$ form a ring system with Z$^1$ and Z$^2$ and R$^3$ and R$^4$ form a ring system with Z$^3$ and Z$^4$, respectively, and
R$^N$ is selected from hydrogen, C$_1$ to C$_{20}$ straight chain, branched chain or cyclic aliphatic hydrocarbons, optionally having one or more unsaturated bonds, C$_3$-C$_8$-heterocycloalkyl or C$_6$ to C$_{20}$ aromatic hydrocarbon and partially arene-hydrogenated forms, each hydrocarbon optionally being substituted by one or more groups selected from C$_1$ to C$_{20}$ straight chain, branched chain or cyclic aliphatic hydrocarbons, optionally having one or more unsaturated bonds, C$_3$-C$_8$-heterocycloalkyl or C$_6$ to C$_{20}$ aromatic hydrocarbon and partially arene-hydrogenated forms,
or its tautomeric forms, or ionic forms.

2. The chiral imidodiphosphate according to claim 1, wherein in formula (I), Z$^1$ to Z$^4$ represent O, n is 1, R$^1$ to R$^4$, R$^N$, X and Y as well as W are as defined as in claim 1, as represented by formula (II):

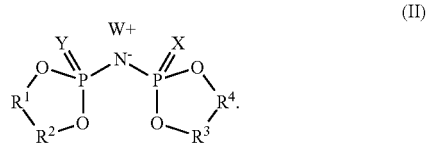

3. The chiral imidodiphosphate according to claim 1, wherein at least one moiety

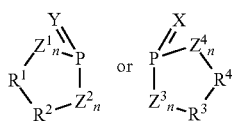

is a five to ten-membered ring structure and $R^1$ to $R^4$, $R^N$, X and Y as well as W are as defined as in claim 1.

4. The chiral imidodiphosphate according to claim 1, wherein, in formula (I), $Z^1$ to $Z^4$ represent O, n is 1, X and Y represent O, $R^1$ to $R^4$ as well as W are as defined as in claim 1, as represented by formula (III):

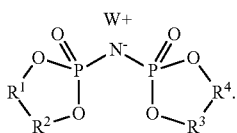

5. The chiral imidodiphosphate according to claim 4, wherein, in such formula (III),
$R^1$ to $R^4$, respectively are selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, and
W is selected from hydrogen, halogen, a metal, or a cationic organic group, or a substituted silicon —$SiR^{'}R^{''}R^{'''}$, wherein $R^{'}$, $R^{''}$ and $R^{'''}$ are same or different and each stand for hydrogen, halogen, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms thereof, or its tautomeric forms, or ionic forms.

6. The chiral imidodiphosphate according to claim 4, wherein, in such formula (III), ($R^1$ and $R^2$) and ($R^3$ and $R^4$), respectively each form a ring structure which is the same or different and is derived from a bridged, optionally dimeric, aromatic structure, or a partially arene-hydrogenated form of such aromatic ring structure, each of said rings systems optionally being substituted by one or more substituents which are the same or different on each position and are selected from hydrogen, heterosubstituents, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, and
W is as defined as in claim 4,
or its tautomeric forms, or ionic forms.

7. The chiral imidodiphosphate according to claim 5, wherein the compound of formula (I) is represented by formula (IV):

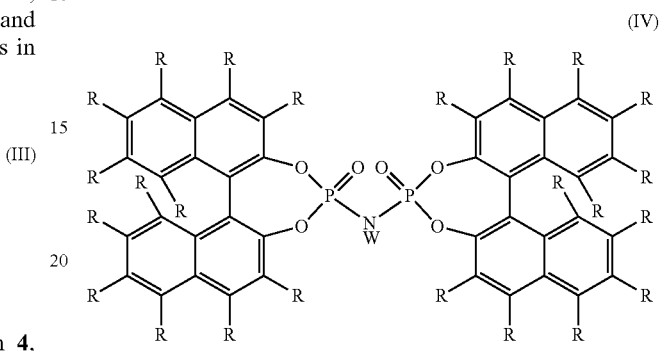

wherein in said formula (IV), the substituent R is same or different on each position and is selected from hydrogen, heterosubstituent, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, and
W has the meaning as defined in claim 5.

8. The chiral imidodiphosphate according to claim 4, wherein at least one of said ring structures formed by ($R^1$ and $R^2$) or ($R^3$ and $R^4$) is chiral, optionally with a $C_2$ symmetry axis.

9. The chiral imidodiphosphate according to claim 4, wherein the ring structures formed by ($R^1$ and $R^2$) or ($R^3$ and $R^4$), respectively, are identical.

10. The chiral imidodiphosphate according to claim 1, as represented by the following formula (IVa):

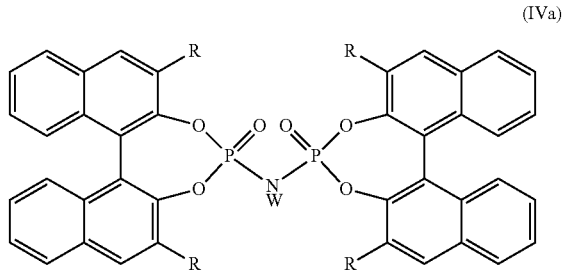

wherein the substituent R is the same or different on each position and is selected from hydrogen, heterosubstituent, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, and W is selected from hydrogen, halogen, a metal, or a cationic organic group, or a substituted silicon —$SiR^IR^{II}R^{III}$, wherein $R^I$, $R^{II}$ and $R^{III}$ are same or different and each stand for hydrogen, halogen, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms thereof, or its tautomeric forms, or ionic forms.

11. The chiral imidodiphosphate according to claim 10, wherein the substituent R is the same on each position.

12. The chiral imidodiphosphate according to claim 1, wherein W is hydrogen.

13. A method comprising conducting an organic synthesis reaction that is catalyzed by a chiral Brønsted acid catalyst, wherein the chiral Brønsted acid catalyst is the chiral imidodiphosphate of the formula (I) according to claim 1.

14. A method comprising conducting a phase-transfer catalysis reaction in the presence of a phase-transfer catalyst, wherein the phase-transfer catalyst comprises the chiral imidodiphosphate of the formula (I) according to claim 1 as a chiral anion.

15. A method comprising conducting an organic synthetic reaction that is catalyzed by a chiral catalyst, wherein the chiral catalyst is the chiral imidodiphosphate of the formula (I) according to claim 1, wherein the organic synthetic reaction is selected from aldol reactions, Mukaiyama-Michael reactions, Michael additions, Mannich reactions, TMSCN additions onto aldehydes and ketones, esterifications, etherifications, pinacol rearrangements, acetalizations, cycloadditions, hydroaminations, hydroalkoxylation, hydrations, haloalkoxylation, haloamination, olefin activations, Friedel-Crafts reactions, epoxide openings, Ritter reactions, nucleophilic substitutions of alcohols, asymmetric ring openings, transfer hydrogenations, alkyne additions, allylations propargylations, reductions, epoxidations, isomerizations, iminium catalysis and enamine catalysis.

16. A process for preparing chiral imidodiphosphates of the formula (V):

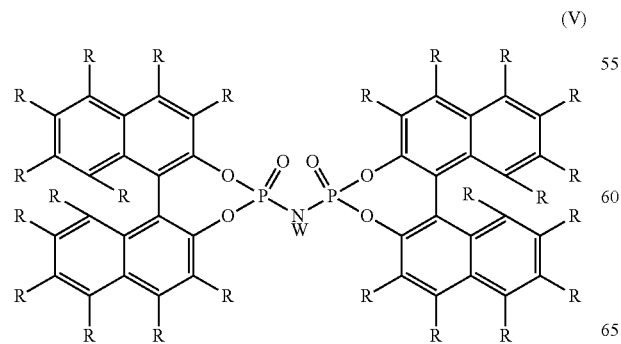

(V)

comprising the steps of reacting a compound of the formula (VI):

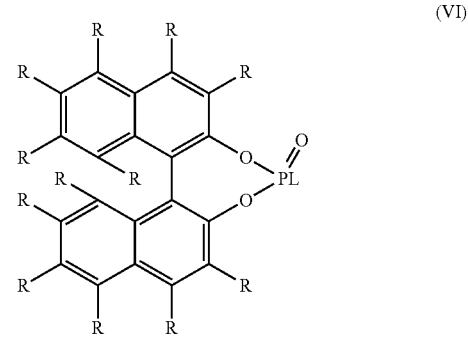

(VI)

in the presence of a basic compound in an organic solvent with a compound of the formula (VII):

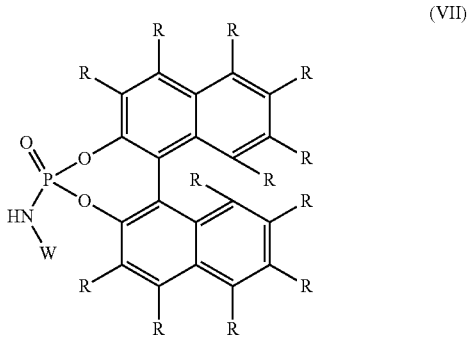

(VII)

to yield said compound of the formula (V);
wherein in said formulae (V), (VI and VII):
L represents a leaving group selected from halogen, alkoxy, aryloxy, heteroaryloxy aryl, heteroaryl, OH, and
wherein the substituent R is the same or different on each position and is selected from hydrogen, heterosubstituent, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, and W is selected from hydrogen, halogen, a metal, or a cationic organic group, or a substituted silicon —$SiR^IR^{II}R^{III}$, wherein $R^I$, $R^{II}$ and $R^{III}$ are same or different and each stand for hydrogen, halogen, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms thereof.

17. The method according to claim 15, wherein the organic synthetic reaction is selected from the group consisting of vinylic aldol reactions, Mukaiyama aldol reactions, transacetalisations, spiro-acetalisations, asymmetric reductions, and olefin metathesis.

* * * * *